United States Patent [19]

Dikstein et al.

[11] 4,419,367

[45] Dec. 6, 1983

[54] STIMULANT

[75] Inventors: Shabtay Dikstein; Mark Segal, both of Jerusalem, Israel

[73] Assignee: Yissum Research Development Company of the Hebrew University of Jerusalem, Jerusalem, Israel

[21] Appl. No.: 123,881

[22] Filed: Feb. 22, 1980

[30] Foreign Application Priority Data

Feb. 27, 1979 [IL] Israel ............................... 56755

[51] Int. Cl.³ .......................................... A61K 31/135
[52] U.S. Cl. ..................................... 424/330; 564/374
[58] Field of Search ......................... 564/374; 424/330

[56] References Cited

U.S. PATENT DOCUMENTS 3,089,826  5/1963  Sahyun et al. ............... 564/374
3,215,738  11/1965  Osbond et al. ............... 564/374

OTHER PUBLICATIONS

*Res. Comm. Psychol. Psychiat. Behav.*, 2, 161, 1977.
*Experientia*, 33, 14301, 1977.
*Res. Comm. Psychol. Psychiat. Behav.*, 3, 359, 1978.
Christians et al., *Bull. Soc. Chim. Biol.*, 79, (1970).
*J. Med. Pharm. Chem.*, 5, 793, (1962).
Zarzecki, P. et al., "Interactions of Nigrostriate Synaptic Transmission, Iontopheric O-methylated Phenethylamines", *Dopamine, Apomorphine and Acetylcholine, Brain Research*, 115, (1976), 257-272.
Ernst, A. M., "Relation Between the Structure of Certain Methoxy-Phenylethylaminederivatives and the Occurrence of a Hypokinetic Rigid Syndrome", *Psychopharmacologia*, 7, 383-390, (1965).
Jacobs, B. L. et al., "Brain Stem and Spinal Cord Mediation of Serotonergic Behavioral Syndrome", *Brain Research*, 100, (1975), 450-457.
Clark, L. C. et al., "The Effects of Ring-Methoxyl Groups on Biological Deamination of Phenethylamines", *J. Med. Chem.*, 8, 353-355, (1965).

*Primary Examiner*—Frederick E. Waddell
*Attorney, Agent, or Firm*—Browdy and Neimark

[57] ABSTRACT

The present invention relates to pharmaceutical and veterinary compositions for use as sex stimulants for mammals which comprise an active ingredient phenylethylamine substituted in the ortho or in the meta position by a methoxy group, a methylthio group, by a chlorine atom or by a bromine atom, as well as salts and complexes of these compounds. The invention further relates to the ortho- and meta- methoxyphenylethylamine and methylthiophenylethylamine compounds and to their salts and complexes as novel compounds.

4 Claims, No Drawings

STIMULANT

FIELD OF THE INVENTION

The invention relates to novel pharmaceutical compositions which are sex stimulants for mammals. This term includes both humans and animals, and more specifically domesticated mammals. Furthermore, the invention relates to certain novel compounds which are of use as active ingredients in such compositions, and to the preparation of these. Further aspects of the invention will become apparent hereinafter.

BACKGROUND OF THE INVENTION

It has been reported (Res. Comm. Psychol. Psychiat. Behav. 2, 161, 1977) that p-methoxyphenylethylamine is effective as sex stimulant when administered to mammals. The administration was during 2 days in large doses, or over a period of two weeks in smaller doses. p-Methoxyphenylethylamine is not suitable for use with humans as it results in changes of the blood pressure. It has been found that when administered i.v. to cats at 0.2 mg/kg, an increase of blood pressure results, while chronic oral administration of 50 mg/kg has a hypotensive effect on uninephrectomized DOCA-saline treated rats. The method used is described in Experientia 33, 1430, 1977.

The method for quantifying sexual stimulation in female rats was described in Res. Comm. Psychol. Psychiat. Behav. 3, 359, 1978.

SUMMARY OF THE INVENTION

According to the present invention there are provided pharmaceutical and veterinary compositions for use as sex stimulants in male and female mammals comprising as active ingredient a compound of the general formula

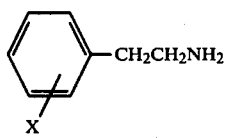

where X designates —OCH$_3$.—SCH$_3$ or a halogen, the substituent being either in ortho or in meta position, as well as the salts and complexes of these. The term halogen in this context designates chlorine or bromine.

The present invention further relates to the compounds defined above, wherein X is —SCH$_3$, both in the ortho and in the meta position, which are novel per se, and to the preparation of these.

The compounds wherein X is methoxy are known compounds, and these were prepared as described in literature. Their physical data are:

| | |
|---|---|
| o-Methoxyphenylethylamine.HCl | M.P. = 138–140° C. |
| m-Methoxyphenylethylamine.HCl | M.P. = 134–141° C. |

The novel thiophenyl derivatives were prepared as follows:

EXAMPLE 1: Preparation of o-Methylthiophenylethylamine.HCl

The compound was prepared according to the following reaction scheme:

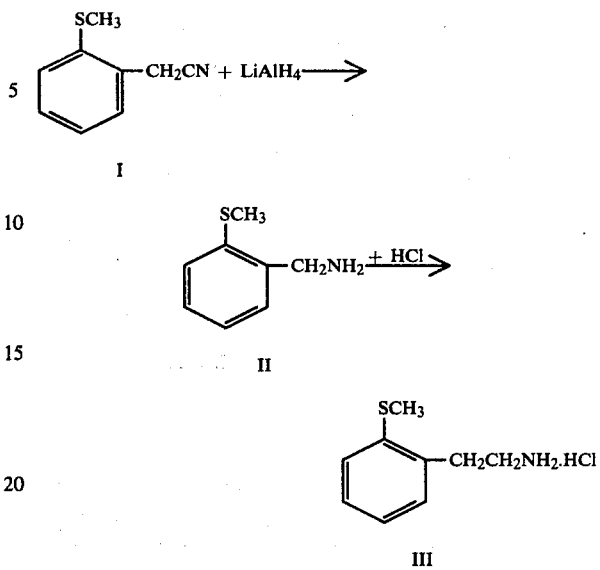

13 g of compound I (Christiaens et al. Bull. Soc. Chim. Belges. 79, 1970, 235-243) dissolved in 50 cc THF was added to a stirred suspension of 5.0 g LiAlH$_4$ so as to maintain a gentle reflux. After stirring overnight at room temperature, the mixture was cooled on an ice bath and water was slowly added, followed by a 20% NaOH solution. The insoluble salts were filtered off, and washed with two portions of ether. The combined filtrates were washed with water and dried over magnesium sulfate. After filtration gaseous HCl was bubbed through for 3 minutes and the resulting yellowish crystals were collected and washed with a little dichloromethane.

Yield: (HCl) 5.5 g. M.P.=165° C.-167° C. (decomp.)

EXAMPLE 2: Preparation of m-Methylthiophenylethylamine

This compound was prepared in a manner corresponding to that of Example 1. Elemental analysis of the hydrochloride salt confirms its composition.

EXAMPLE 3: Preparation of ortho-and meta-halogen substituted compounds

These compounds were prepared as described in J.Med.Pharm.Chem. 5, 793 (1962). The orth-chloro, meta-chloro, ortho-bromo and meta-bromo compounds were tested on animals and all of these were found to be effective sex stimulants.

Results of Animal Tests:

Typical results are presented in Table 1 which demonstrates the drastic difference between the ortho- and the meta-derivatives versus the para-derivative.

The compounds of the present invention have no adverse side effect on the blood pressure of rats on oral administration. The compounds were tested on DOCA-saline treated rats and, even at 50 mg/kg per day for a week, no effect on blood pressure was observed.

The compounds can be used as such, or in the form of physiologically acceptable salts or complexes. The pharmaceutical composition can be administered in the form of sustained release preparations or as implants.

Preliminary tests with human volunteers have shown that the pharmaceutical compositions of the present invention exert a pronounced effect on human males.

Tests have shown that o-methoxy- and o-methylthio-phenylethylamine are effective in dosages of 35 to 50 mg when given per os as the hydrochloride salt. A preferred dose is in the range of from 5 to 10 mg, a number of times per day. The drug is advantageously administered per os in the form of capsules. The effect is obtained after a few hours to a few days.

There may be used the free base, any pharmaceutically acceptable salt or complex.

TABLE 1

Effect of Sustained Administration of Methoxy- and Methylthiophenylethylamines*
on the Sexual Behavior of Rats

| Treatment | Minimal effective oral dose mg/kg/day | Male mountings/animal in first 15 minutes | Female lordosis/mount coefficient |
|---|---|---|---|
| Control | — | 1 ± 1 | 0.1 ± 0.03 |
| o-Methoxyphenylethylamine | 0.25 | 20 ± 4 | 0.5 ± 0.05 |
| o-Methylthiophenylethylamine | 0.25 | 25 ± 5 | 0.5 ± 0.05 |
| m-Methoxyphenylethylamine | 1.00 | 20 ± 4 | 0.5 ± 0.05 |
| m-Methylthiophenylethylamine | 1.00 | 20 ± 4 | 0.5 ± 0.05 |
| p-Methoxyphenylethylamine | 10.00 | 10 ± 2 | 0.3 ± 0.05 |
| p-Methylthiophenylethylamine | 10.00 | 10 ± 3 | 0.3 ± 0.05 |
| o-Chloro-phenylethylamine | 10.00 | 10 ± 2 | 0.3 ± 0.05 |

*as hydrochloride salts

We claim:

1. A method for stimulating the sex drive in mammals, comprising administering an effective amount of a compound of the formula

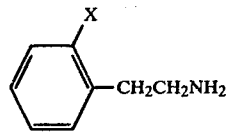

wherein X comprises a methoxy or methylthio group, or a pharmaceutically acceptable acid addition salt thereof.

2. A method in accordance with claim 1, wherein said pharmaceutically acceptable acid addition salt is the hydrochloric acid addition salt.

3. A method in accordance with claim 1, wherein said compound is o-methoxyphenylethylamine or a pharmaceutically acceptable acid addition salt thereof.

4. A method in accordance with claim 1, wherein said compound is o-methylthiophenylethylamine or a pharmaceutically acceptable acid addition salt thereof.

* * * * *